United States Patent [19]

Zawalski

[11] Patent Number: 5,017,732
[45] Date of Patent: * May 21, 1991

[54] PROCESS FOR PREPARING CHLOROFLUOROCARBONS VIA AN IN SITU GENERATED ACTIVATED ALUMINUM TRIHALIDE CATALYST AND PRODUCTS RESULTING THEREFROM

[75] Inventor: Robert C. Zawalski, Houston, Tex.

[73] Assignee: Dixie Chemical Company, Pasadena, Tex.

[*] Notice: The portion of the term of this patent subsequent to May 15, 2007 has been disclaimed.

[21] Appl. No.: 480,744

[22] Filed: Feb. 16, 1990

[51] Int. Cl.$^5$ .................. C07C 17/24; C07C 19/08; B01J 31/00
[52] U.S. Cl. .................. 570/151; 502/151; 570/163
[58] Field of Search .................. 570/151; 502/151

[56] References Cited

U.S. PATENT DOCUMENTS

| | | | |
|---|---|---|---|
| 2,598,411 | 5/1952 | Miller et al. | 570/151 |
| 3,398,202 | 8/1968 | Foulletier | 260/653 |
| 3,787,331 | 1/1974 | Groppelli et al. | 252/442 |
| 4,748,284 | 5/1988 | Gozzo et al. | 570/151 |
| 4,925,993 | 5/1990 | Zawalski | 570/151 |

FOREIGN PATENT DOCUMENTS 0317981 5/1989 European Pat. Off. .
2245372 3/1974 Fed. Rep. of Germany .

*Primary Examiner*—J. E. Evans
*Attorney, Agent, or Firm*—Pravel, Gambrell, Hewitt, Kimball & Krieger

[57] ABSTRACT

A process for isomerizing a chlorofluorocarbon of the formula:

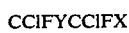

wherein X and Y are independently selected from chlorine and fluorine provided that X is not —Cl when Y is —F
to the compound of the formula:

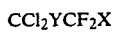

The process comprises contacting the chlorofluorocarbon with an activated aluminum trihalide catalyst. The catalyst is prepared by contacting the chlorofluorocarbon with anhydrous aluminum trichloride in the presence of a metal. The metal is selected from the group consisting of stainless steel, chromium, manganese, molybdenum, tungsten and combinations thereof.

23 Claims, No Drawings

PROCESS FOR PREPARING CHLOROFLUOROCARBONS VIA AN IN SITU GENERATED ACTIVATED ALUMINUM TRIHALIDE CATALYST AND PRODUCTS RESULTING THEREFROM

FIELD OF THE INVENTION

This invention relates to activated aluminum trihalide catalysts and the process of isomerizing chlorofluorocarbons in the presence of such in situ produced catalysts. The use of the activated catalyst in the isomerization process renders a product mixture having negligible non-isomerized material.

BACKGROUND OF THE INVENTION

Chlorofluorocarbons have been widely used in industry as refrigerants and aerosols. When released into the atmosphere, the accumulation of such chlorofluorocarbons can eventually cause depletion of the ozone layer. Many countries have barred the use of $CCl_2F_2$ and $CCl_3F$ due to their ability to reach the stratosphere. The industry has focused on the use of perfluorocarbons, tetrafluoroethanes and chlorofluorohydrocarbons in recent years since these compounds are believed not to significantly contribute to ozone depletion. Of particular interest to the refrigerant industry is 1,1,1,2-tetrafluoroethane. Such compounds can be derived from the intermediates 1,1-difluorotetrachloroethane, 1,1,1-trifluorotrichloroethane and 1,2,2,2-tetrafluorodichloroethane. These intermediates are, in turn, the isomers of the more readily obtainable chlorofluoroethanes 1,2-difluoro-1,1,2,2-tetrachloroethane, 1,1,2-trifluoro-1,2,2-trichloroethane and 1,1,2,2-tetrafluoro-1,2,-dichloroethane, respectively.

The isomerization of such chlorofluoroethanes by treatment with aluminum trihalide is well documented in the art. For example, Okuhara in 23 *J. Org. Chem* 2745 (1977) reports the use of aluminum trihalide and an inert solvent for isomerizing 1,1,2-trichloro-1,2,2-trifluoroethane. Unfortunately, the prior art methods render a high amount of starting material in the final reaction mixture. This is evidenced in, for example, German Patent No. 1,668,346 which discloses an isomerization method for the production of 1,1,1-trifluorotrichloroethane. This process involves the preactivation of an aluminum chloride catalyst with 1,1,2-trifluorotrichloroethane at 30° to 60° C., subsequent cooling and then addition of new starting material. The amount of starting material in the final reaction mixture is from about 2% to 10%. As the boiling point of starting material and the desired isomerized product are roughly the same, conventional distillation techniques can not be employed to separate the compounds.

Alternative methods for obtaining the isomerized product with negligible amounts of non-isomerized starting material are therefore needed.

Summary of the Invention

The invention comprises a process of isomerizing chlorofluoroethane intermediates of 1,1,1,2-tetrafluoroethane. In particular, the process comprises isomerizing the chlorofluorocarbons 1,2-difluoro-1,1,2,2-tetrachloroethane, 1,1,2-trifluoro-1,2,2-trichloroethane and 1,2,2-tetrafluoro-1,2-dichloroethane in the presence of an activated aluminum trihalide catalyst. The amount of non-isomerized chlorofluorocarbon in the product mixture is generally negligible.

The activated aluminum trihalide catalyst is generated in situ in the isomerization reaction vessel containing 1,1,1,2-tetrafluoroethane intermediate, the anhydrous aluminum trichloride and a metal. The metal is either a metal powder or an elemental metal of a member selected from the group consisting of chromium, manganese, molybdenum, tungsten and stainless steel and combinations thereof. The metal may be added directly to the reaction vessel. Alternatively, where the desired metal is stainless steel, the metal may be leached from the vessel. A catalytic heel containing the in situ generated aluminum trihalide catalyst can be separated from the product mixture.

DESCRIPTION OF THE PREFERRED EMBODIMENTS

The invention is drawn to a process of isomerizing chlorofluorocarbons useful as intermediates in the production of 1,1,1,2-tetrafluoroethane. In particular, the invention is drawn to a process of isomerizing the chlorofluorocarbons 1,2-difluoro-1,1,2,2-tetrachloroethane, 1,1,2-trifluoro-1,2,2-trichloroethane and 1,1,2,2-tetrafluoro-1,2-dichloroethane, generically represented by the formula:

$$\text{CClFYCClFX} \qquad (I)$$

wherein X and Y independently are selected from the group consisting of —Cl and —F, provided that X is not —Cl when Y is —F to the product of the formula:

$$\text{CCl}_2\text{YCF}_2\text{X} \qquad (II)$$

The chlorofluorocarbon of formula I is most preferably either $CCl_2FCClF_2$ or $CClF_2CClF_2$.

The process comprises contacting the di-, tri- or tetrafluorochlorocarbon of formula (I) with anhydrous aluminum trichloride and metal. An activated aluminum trihalide is generated in the process. The high yields of isomerized product produced in this invention are attributed to this in situ generated activated catalyst.

The weight ratio of the chlorofluorocarbon of formula (I) to aluminum trichloride is approximately between from about 16:1 to about 150:1, most preferably 30:1.

To the compound of formula (I) and aluminum trichloride is added a metal. The metal may be either an elemental metal or a metal powder. The metal is selected from stainless steel or chromium, manganese, molybdenum, tungsten and combinations thereof. The mesh of the metal normally ranges from about −200 to about −300. Preferably a mixture of metals having a weight ratio of 99:1 to 1:99, particularly 1:3 to 3:1, is employed. Most preferably, the mixture comprises chromium and manganese. The aluminum trichloride: metal weight ratio is between from about 200:1 to 2000:1, most preferably about 600:1.

Where the reaction is conducted in a stainless steel, instead of a glass, vessel the requisite metal may be leached into the reaction vessel. In such instances, it may be desired to add an additional metal in order to ensure the desired $AlCl_3$: metal weight ratio.

The introduction of the chlorofluorocarbon of formula (I), anhydrous aluminum trichloride and metal to the reaction vessel generates in situ an aluminum trihalide catalyst to which the high yields of the desired isomer in the product mixture is attributed. Experimental data on the conversion of 1,1,2,2-tetrafluorodichloroethane to 1,2,2,2-tetrafluorodichloroethane indicates halogen exchange between the chlorofluorocarbon and AlCl₃. The presence of CF₃CCl₃ and the absence of the disproportionation product CF₃CF₂Cl in the product mixture supports the following reaction:

$$3CClF_2CClF_2 + AlCl_3 \rightarrow 3CCl_3CF_3 + AlF_3$$

The isomerization process of this invention is conducted at a temperature above the melting point of the desired isomerized product. The reaction is generally allowed to proceed until the amount of reactant of formula (I) in the reaction mixture is less than 45,000 ppm. Where the 1,2-difluoro- and 1,1,2-trifluoro-intermediates are the compounds being isomerized, the isomerization may generally be permitted to proceed until less than 10,000 ppm of the non-isomerized compound constitutes the product mixture. Following isomerization, the reaction vessel is cooled to a temperature slightly above the melting point of the desired isomerized product. The activated aluminum trihalide is allowed to settle to the bottom of the reaction vessel. Upon settling, the organic media is decanted allowing for recovery of the catalyst. A thin layer of organic media, generally between about 10 to about 20 weight percent, is permitted to remain with the catalyst. This thin layer of organic media and catalyst, hereinafter collectively referred to as the "catalytic heel", prevents water vapor from contaminating the catalyst and further facilitates the removal of spent catalyst from the reactor as a fine slurry. By not siphoning off all of the available crude product produced in a given batch, loss of finely divided catalyst is kept to a minimum. Normally 10 to 20 weight percent of the product mixture is allowed to remain as a slurry with the catalyst to form the catalytic heel.

When the difluoro- and trifluoro intermediates are isomerized, the reaction temperature ranges generally between about 36° to about 52° C. When the intermediate is the difluoro intermediate, i.e. X and Y of formula (I) are both —Cl, the reaction temperature is preferably between about 44° and 50° C. When the intermediate is the trifluoro intermediate, i.e., X and Y of formula (I) are chlorine and fluorine, respectively, the reaction temperature is preferably from about 45° C. to about 51° C. The difluoro and trifluoro intermediates preferably are generally allowed to isomerize until the amount of non-isomerized reactant of formula (I) is minimal, usually less than about 10,000 ppm. The reaction vessel is cooled to about 2° to about 5° C. above its melting point, wherein the catalyst derivative settles to the bottom of the reactive vessel. Cooling of the reaction vessel is preferably from about 17° to about 30° C. when the trifluoro intermediate is isomerized and about 42° to about 44° C. when the difluoro intermediate is isomerized.

When the tetrafluoro intermediate (wherein X and Y of formula (I) are both —F) is isomerized, the reaction temperature is generally between about 120° and about 130° C., i.e., about 15° to 25° C. below the critical temperature of the reactant of formula (I). The organic media is decanted after the reaction vessel is cooled to a temperature between about −20° C. and about −10° C.

The isomerization normally proceeds at atmospheric pressure. However, since the autocatalytic reaction between anhydrous aluminum trihalide and certain chlorofluorocarbons, such as CCl₂FCClF₂, can be violent, especially at high temperatures under adiabatic conditions, the activation process may be performed in a suitable high pressure vessel.

Separation of the trace amount of (non-isomeric) by-products from the organic phase then proceeds by techniques well known to those skilled in the art, such as distillation.

The non-isomerized reactant of formula (I) after being separated from the organic phase may be reintroduced to fresh anhydrous aluminum trichloride and metal and isomerization repeated under the conditions recited herein.

The catalytic heel comprising the in situ generated activated aluminum trihalide catalyst may further be used to isomerize a fresh sample of 1,2-difluoro-, 1,1,2,2-tetrachloroethane or 1,1,2-trifluoro-1,2,2-trichloroethane. The catalytic heel generated in a reaction vessel containing either the di-, tri- or tetrafluorochlorocarbon of formula (I) may serve as the activated aluminum trihalide catalyst in the isomerization of this (second) fresh sample of di- and trifluorochlorocarbon. It is not necessary that the activated aluminum trihalide catalyst employed in the second isomerization reaction be generated in a product mixture comprising the chlorofluorocarbon sought to be isomerized. For example, if the desired isomerized product is that obtained from the process:

$$CCl_2FCClFX \quad (IV)$$

$$\rightarrow$$

$$CCl_3CF_2X \quad (V)$$

wherein X is either —Cl or —F, the activated aluminum trihalide catalyst may be generated from either the di, tri-, or tetrafluoro-intermediate. In other words, a catalytic heel obtained from the isomerization of the 1,2-difluoro- or 1,1,2,2-tetrafluoro, as well as that obtained from the 1,1,2 trifluoro-, intermediate may be used as the activated aluminum trihalide catalyst for the isomerization of the 1,1,2-trifluoro intermediate. Similarly, the catalytic heel obtained from the isomerization of the 1,1,2-trifluoro or 1,1,2,2-tetrafluoro, as well as the 1,2-difluoro, intermediate can be used as the activated aluminum trihalide catalyst for the isomerization of a 1,2,-difluoro intermediate. Such isomerizations employing catalytic heel as activated aluminum trihalide catalyst are generally terminated when the amount of chlorofluorocarbon of formula (IV) in the reaction vessel is less than about 15,000 ppm. Preferably, the catalyst is terminated when the non-isomerized product, such as that of formula (IV) wherein X is —F, is less than 400 ppm. Such conversion normally requires from about 2 hours to about 24 hours, most often 8 hours.

The activated trihalide catalyst may be reused until the catalyst no longer effectively renders an isomerized product mixture containing less than 450 ppm non-isomerized chlorofluorocarbon. The process is repeated by adding approximately an equivalent weight amount of fresh chlorofluorocarbon (to that weight amount of product mixture removed) to the catalytic heel. Following the removal of the resulting catalytic heel from each isomerization, the organic phase of each isomerization can be pooled together. The separation of desired isomers, by such conventional techniques as distillation, from the organic phases can then be collectively performed.

In general, the weight ratio of chlorofluorocarbon to activated aluminum trihalide catalyst is greater than 16:1. Since the life span of the catalyst decreases as this ratio increases, commercial practicality dictates this ratio to be probably not greater than 80:1.

The activated aluminum trihalide derivative may further be used to isomerize that portion of the nonisomerized reactant of formula (I) separated from the desired isomer of the product mixture.

EXAMPLE 1

To a 5.0 l glass flask equipped with motor stirrer, thermometer, heating mantle, and reflux condenser with drying tube, was charged 120 g of anhydrous aluminum chloride powder and 6.0 g of PROPACK (a square 0.16 inch 316 stainless steel protruded packing). To the flask was added 3,900 g of $CCl_2FCClF_2$ and vigorous agitation was applied. The mixture was heated to 49°–50° C. (reflux) for 8 hours. Gas chromatography analysis indicated 3,846 ppm $CCl_2FCClF_2$.

The mixture was allowed to stand for 2 hours to allow settling of the catalyst. Crude isomerized $CCl_3CF_3$ product was then carefully siphoned off (2,750 g) leaving the active catalyst heel in the bottom of the flask (with a liquid level up to the agitator blades).

EXAMPLE 2

The heating mantle was removed from the 5.0 l flask (example 1), and an adjustable ice bath and addition funnel were added. Over a period of 40 min., 2,750 g of fresh $CCl_2FCClF_2$ was added to the agitated mixture. Reaction temperature was maintained at 22° to 28° C. Upon completion of the addition, the mixture was stirred at 20° C. for 3.5 hours after which gas chromatography analysis indicated only 366 ppm $CCl_2FCClF_2$ remaining.

Agitation was stopped for 2 hours to allow settling of the catalyst bed. The $CCl_3CF_3$ product was siphoned off (2,750 g) and the process repeated (see Table 1).

TABLE 1

| \multicolumn{4}{c}{ISOMERIZATIONS FROM 316SS ACTIVATED $AlCl_3$} |
| Cycle No. | $CCl_2FCClF_2$ Reacted (g) | Reaction Time (hrs.) | $CCl_2FCClF_2$ Unreacted, ppm |
| --- | --- | --- | --- |
| 1 | 2750 | 3 | 377 |
| 2 | 2750 | 3 | 334 |
| 3 | 2900 | 3 | 341 |
| 4 | 2750 | 3 | 320 |
| 5 | 2800 | 3 | 323 |
| 6 | 2800 | 3 | 309 |
| 7 | 2900 | 3 | 469 |
|   |      | 4 | 332 |
| 8 | 2800 | 4 | 935 |
|   |      | 6 | 342 |
| 9 | 2600 | 3 | 23,000 |
|   |      | 6 | 1,200 |
|   |      | 8 | 406 |

EXAMPLE 3

A 5.0 l flask fitted with motor stirrer, thermometer, heating mantle, and reflux condenser with drying tube, was charged with 96.1 g of anhydrous aluminum trichloride powder, 0.1198 g chromium powder (−200 mesh), 0.0409 g of manganese powder (−325 mesh), and 3,044.5 g of $CCl_2FCClF_2$.

With vigorous agitation, the flask was brought to reflux for 6 hours (48° C.). The mixture was then allowed to agitate for 15 hours at 23°–26° C. At this time the amount of non-isomerized $CCl_2FCClF_2$ had been reduced to 18,400 ppm (IR analysis). The mixture was then brought back to reflux for 7 hours, and then cooled to 27° C. After allowing the catalyst to stand for 16 hours, the amount of non-isomerized $CCl_2FCClF_2$ had dropped to 4,551 ppm (g.c. analysis). The crude product (2127 g) was carefully decanted to avoid disturbing the active catalyst heel.

EXAMPLE 4

The 5.0 l flask (example 3) was fitted with an adjustable ice bath and addition funnel. To the flask was added 2,505 g of fresh $CCl_2FCClF_2$ and agitation begun. Temperature was maintained between 20° and 32° C. After 7 hours reaction, crude product was found to contain 367 ppm $CCl_2FCClF_2$. The catalyst was permitted to settle for 2 hours and 2,100 g of crude $CCl_3CF_3$ product carefully decanted. The process was repeated for a total of 19 cycles (see Table 2).

TABLE 2

| \multicolumn{4}{c}{ISOMERIZATION REACTIONS FROM Cr/Mn PROMOTED $AlCl_3$} |
| Cycle No. | $CCl_2FCClF_2$ Reacted (g) | Reaction Time (hrs.) | $CCl_2FCClF_2$ Unreacted, ppm |
| --- | --- | --- | --- |
| 1 | 2505 | 7 | 367 |
| 2 | 2505 | 6 | 310 |
| 3 | 2511 | 3 | 311 |
| 4 | 2400 | 3 | 337 |
| 5 | 2552 | 3 | 320 |
| 6 | 2513 | 3 | 361 |
| 7 | 2512 | 3 | 296 |
| 8 | 2512 | 3 | 333 |
| 9 | 2532 | 3 | 333 |
| 10 | 2506 | 3 | 348 |
| 11 | 2526 | 3 | 368 |
| 12 | 2548 | 4 | 356 |
| 13 | 2507 | 3 | 376 |
| 14 | 2476 | 3 | 334 |
| 15 | 2544 | 3 | 423 |
|    |      | 5 | 352 |
| 16 | 2509 | 3 | 1331 |
|    |      | 5 | 329 |
| 17 | 2524 | 3 | 1184 |
|    |      | 5 | 344 |
| 18 | 2503 | 3 | 4118 |
|    |      | 5 | 495 |
| 19 | 2524 | 3 | 11900 |
|    |      | 5 | 952 |

EXAMPLE 5

To a 2.0 l Parr bomb equipped with glass liner and tempered water heating coil was charged 1,000 g of $CCl_2FCClF_2$, 33.3 g of anhydrous aluminum trichloride, 0.04 g of powdered chromium, and 0.01 g of powdered manganese. With vigorous agitation, the mixture was heated from 20° to 50° C. in 42 minutes and pressure was slowly increased. An exotherm then developed which elevated the temperature to 90° C. within 10 minutes and increased pressure to 45 psig. The mixture was allowed to cool and catalyst allowed to settle. The catalytic heel was collected from the mixture.

EXAMPLE 6

An insulated beaker with stirrer was charged with 43.5 g of previously prepared catalyst heel (example 5). To the beaker was added 20.2 g of $CCl_2FCClF_2$ and agitation begun. Within 14 minutes, the temperature was allowed to climb from 19° C. until it reached a maximum of 35° C. After 22 minutes stirring, the mixture was sampled and found to contain 92.25% converted $CCl_3CF_3$ (g.c. analysis).

EXAMPLE 7

A 5.0 l flask fitted with a motor stirrer, heating mantle, thermometer, and reflux condenser with drying tube was charged with 120.5 g of anhydrous aluminum trichloride, 0.061 g of powdered manganese (−325 mesh), and 4,008 g of $CCl_2FCClF_2$.

With vigorous agitation, the mixture was heated to reflux for 5 hours (49° C.). Heating was then discontinued and the mixture stirred an additional 13 hours at 28° to 22° C. Gas chromatography analysis indicated approximately 660 ppm of $CCl_2FCClF_2$ in the product mixture. After allowing the catalyst to settle for 2 hours, the crude isomerized product was siphoned off (3100 g), leaving the catalyst in the bottom of the flask.

EXAMPLE 8

The 5.0 l flask (example 7) was fitted with an adjustable ice bath and addition funnel. Within 20 minutes, 3100 g of fresh $CCl_2FCClF_2$ was charged (vigorous agitation). After 2.5 hours stirring at 18° to 34° C., the amount of $CCl_2FCClF_2$ in the reaction mixture was approximately 446 ppm. After standing an additional 15 hours, the concentration was 410 ppm. The crude product was then siphoned off (3100 g) and the process repeated with the resulting catalytic heel and fresh $CCl_2FCClF_2$ (See Table 3).

TABLE 3

| ISOMERIZATION REACTIONS OF Mn PROMOTED $AlCl_3$ | | | |
|---|---|---|---|
| Cycle No. | $CCl_2FCClF_2$ Added/g | Reaction Time (hrs.) | $CCl_2FCClF_2$ Unreacted, ppm |
| 1 | 3100 | 2.5 | 446 |
|   |      | 17.5 | 410 |
| 2 | 3200 | 2.0 | 326 |
| 3 | 3083 | 3.5 | 710 |
|   |      | 21.0 | 345 |

EXAMPLE 9

A 2.0 l 4-neck flask fitted with motor stirrer, thermometer, and reflux condenser with drying tube was charged with 23.5 g of the resulting catalyst heel prepared as in Example 3. To the flask was added 256.5 g of $CCl_2FCCl_2F$ and agitation begun. During the first 1.5 hours of stirring the temperature increased from 28° to 34° C. Since the solid product was starting to precipitate, the flask temperature was adjusted to 42° C. and the mixture was then stirred for 2.5 hours. The IR spectrum of the reaction mixture was consistent with nearly total conversion to $CCl_3CClF_2$.

EXAMPLE 10

A pyrex glass liner from a 2.0 l Parr bomb reactor was charged with 50.0 g of anhydrous aluminum trichloride, 0.065 g chromium and 0.023 g of manganese powder. The pyrex liner was chilled on dry ice and quickly charged with 900 g. of pure $CClF_2CClF_2$. The liner was inserted into the reactor which was immediately sealed. With vigorous agitation, the reactor temperature was brought to approximately 120° C. (277 psig) within 30 minutes. For an additional hour, the temperature was maintained between 120° and 130° C. (to 303 psig).

The mixture was gradually cooled to −10° C. and agitation shut off. The reactor was disassembled to allow direct sampling of the liquid phase. The catalytic heel was separated from the product mixture. Gas chromatographic analysis indicated the product mixture had a composition of 0.719% $CF_3CF_2Cl$, 72.67% $C_2Cl_2F_4$, 26.6% $CCl_3CF_3$ (including a trace of $CCl_2FCClF_2$), 0.006% $CCl_3CClF_2$ and 0.006% $CCl_3CCl_2F$. A gas chromatographic isomer resolution technique determined the ratio of $CCl_2FCF_3/CClF_2CClF_2$ to be 9.64:1.

EXAMPLE 11

The pyrex liner of the 2.0 l Parr bomb was charged with 100.0 g of anhydrous $AlCl_3$, 0.130 g of chromium, and 0.050 g. of manganese powder. After chilling on dry ice, the liner was charged with 900 g. of pure $CClF_2CClF_2$, placed inside the steel reactor and sealed. With the agitator on, heat was applied to raise the temperature to 127° C. in 30 minutes. Thereafter, the temperature was maintained at 127° to 142° C. (to 233 psig) for 6 hours. The mixture was gradually cooled to −10° C. and agitation shut off. The catalytic heel was separated from the product mixture.

Gas chromatographic and FTIR analysis of the liquid phase was consistent with 1.00% $CF_3CF_2Cl$, 51.98% $C_2Cl_2F_4$, 46.71% $CCl_3CF_3$ (2054 ppm $CClF_2Cl_2F$), 0.24% $CCl_3CClF_2$, 0.002% $CCl_3CCl_2F$ and 0.005% $C_2Cl_6$. The ratio of $CCl_2FCF_3/CF_2ClCF_2Cl$ was determined to be 32.56:1.

EXAMPLE 12

The pyrex liner of a 2.0 l Parr bomb was charged with 50.0 g. of anhydrous aluminum trichloride, chilled on dry ice and charged with 900 g. of pure $CClF_2CClF_2$. After sealing the reactor, agitation was begun and contents were brought to 100° C. within one hour. Over the next 30 minutes, the temperature was increased to 120° C. For 3.5 hours thereafter, the temperature was maintained between 120° and 135° C. (268-326 psig).

The reactor was gradually cooled to −10° C. and agitation shut off to permit sampling of the liquid phase. The catalytic heel was separated from the product mixture.

Gas chromatographic analysis indicated only 4.12% of starting material was converted to $CCl_3CF_3$. FTIR analysis indicated no formation of $CF_3CFCl_2$. No other products were detected.

EXAMPLE 13

A 3.0 g sample of the catalytic heel from example 10 was treated in a 10 ml test tube with 9.4 g of $CCl_2FCClF_2$ and vigorously agitated. Within 4 minutes, the temperature climbed from 22° to 42° C. The resulting catalytic heel was separated from the product mixture. Gas chromatographic analysis one hour after initial mixing indicated only 320 ppm $CCl_2FCClF_2$ (major product=$CCl_3CF_3$).

EXAMPLE 14

The Parr bomb reaction mixture (from example 11) was chilled to −10° C. and approximately 800 g of crude product was siphoned off, leaving the catalytic heel intact. A charge of 900 g. of pure $CClF_2CClF_2$ was quickly added and the Parr bomb resealed.

After approximately 4 hours heating to 131° C. (229 psig) FTIR analysis indicated no observable isomerization to $CF_3CFCl_2$.

The invention has been described with reference to its preferred embodiments. Those of ordinary skill in the art may, upon reading this disclosure, appreciate changes or modifications which do not depart from the scope and spirit of the invention as described above or claimed hereafter.

I claim:

1. An activated aluminum trihalide catalyst prepared by the process comprising:
   (i) contacting the chlorofluorocarbon 1,1,2,2-tetrafluoro-1,2-dichloroethane with anhydrous aluminum trichloride in the presence of a metal for a time and at a temperature sufficient for said chlorofluorocarbon to isomerize to 1, 2, 2, 2- tetrafluorodichloroethane;
   (ii) removing at least the majority of the organic layer from the product mixture of step (i); and
   (iii) recovering the catalytic heel therefrom.

2. The product of claim 1, wherein the weight ratio of chlorofluorocarbon to aluminum trichloride is between from about 16:1 to about 80:1.

3. The product of claim 1, wherein said metal is selected from the group consisting of chromium, manganese, molybdenum, tungsten, stainless steel and combinations thereof.

4. The product of claim 3, wherein said process is conducted in a stainless steel reactor vessel and said metal is leeched from said vessel.

5. The product of claim 1, wherein the weight ratio of aluminum trichloride to metal is from about 200:1 to about 2000:1.

6. The product of claim 3, wherein said metal is a mixture of chromium and manganese.

7. The product of claim 1, wherein said chlorofluorocarbon is contacted with said aluminum trichloride and said metal for a time sufficient for said chlorofluorocarbon to be less than 45,000 ppm.

8. A process for isomerizing chlorofluorocarbons comprising:

(i) contacting a chlorofluorocarbon of the formula:

  CClFYCClFX        (I)

wherein
   X is —Cl or —F when Y is —Cl; or
   X is —F when Y is —F
   with anhydrous aluminum trichloride and a metal for a time and at a temperature sufficient for the compound of formula (I) to isomerize to the compound of formula $CCl_2YCF_2X$ (II);
   (ii) separating at least the majority of the organic phase from the activated aluminum trihalide catalyst; and
   (iii) isolating the isomerized chlorofluorocarbon of formula (II) from the separated organic phase.

9. The process of claim 8, wherein said metal is selected from the group consisting of stainless steel, chromium, manganese, molybdenum, tungsten and combinations thereof.

10. The process of claim 9, wherein X and Y are both —F.

11. The process of claim 10, wherein said metal is a mixture of chromium and manganese.

12. The process of claim 8, wherein the weight ratio of aluminum trichloride to metal is from about 200:1 to about 2000:1.

13. The process of claim 8 wherein said chlorofluorocarbon is contacted with said aluminum trichloride and said metal for a time sufficient for said chlorofluorocarbon to be less than 45,000 ppm.

14. The process of claim 8, further comprising subsequent to step (ii)
    (1) contacting with the catalytic heel of step (ii), a chlorofluorocarbon of the formula:

  CCl_2FCClFX        (III)

wherein X is —Cl or —F;
    for a time and at a temperature sufficient for the chlorofluorocarbon of formula (III) to isomerize to a compound of the formula: $CCl_3CF_2X$ (IV)
    (2) separating the organic phase from the resulting catalytic heel of step (1); and
    (3) isolating the isomerized chlorofluorocarbon of formula (IV) from the separated organic phase.

15. The process of claim 14, further comprising subsequent to step (2) successively repeating steps (1) through (2).

16. The process of claim 15, wherein the organic phases separated in repetitive steps (2) are pooled together after each completion of step (2).

17. The process of claim 14, wherein the weight ratio of chlorofluorocarbon to catalytic heel in step (1) is between from about 16:1 to about 80:1.

18. The process of claim 14, wherein said chlorofluorocarbon of formula (III) is contacted with said catalytic heel for a time sufficient for the amount of said chlorofluorocarbon (III) to be less than 15,000 ppm.

19. The process of claim 14, wherein X of the compound of formula (III) is —F.

20. The process of claim 19, wherein both X and Y of the compound of formula (I) are —F.

21. The process of claim 14, wherein X of the compound of formula (III) is —Cl.

22. The process of claim 21, wherein both X and Y of the compound of formula (I) are —F.

23. The process of claim 8 wherein X is —F and Y is —Cl.

* * * * *

UNITED STATES PATENT AND TRADEMARK OFFICE
CERTIFICATE OF CORRECTION

PATENT NO. : 5,017,732

DATED : MAY 21, 1991

INVENTOR(S) : ROBERT C. ZAWALSKI

It is certified that error appears in the above-identified patent and that said Letters Patent is hereby corrected as shown below:

Title Page:
In the Abstract, line 1, please delete "for" and insert --of--.

In Col. 1, line 12; Col. 2, lines 4, 13, 44 and 68; and Col. 4, line 16, "in situ" should be italicized.

In Col. 3, line 39, insert a dash after "trifluoro."

In Col. 6, line 24, Table 2, the title after "PROMOTED" delete "$AlCl_2$" and insert --$AlCl_3$-- therefor.

Signed and Sealed this

Eighth Day of December, 1992

Attest:

DOUGLAS B. COMER

*Attesting Officer*　　*Acting Commissioner of Patents and Trademarks*